US006270794B1

(12) United States Patent
Cilento et al.

(10) Patent No.: US 6,270,794 B1
(45) Date of Patent: Aug. 7, 2001

(54) METHOD AND COMPOSITION FOR ABSORBING WOUND FLUIDS

(75) Inventors: Rodolfo D. Cilento, North Brunswick; Laura Lee Bolton, Metuchen, both of NJ (US); Louis A. Pirone, Yardley, PA (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 08/371,042

(22) Filed: Jan. 10, 1995

Related U.S. Application Data

(63) Continuation of application No. 08/198,026, filed on Feb. 17, 1994, now abandoned, which is a continuation-in-part of application No. 07/990,719, filed on Dec. 15, 1992, now abandoned, which is a continuation-in-part of application No. 07/697,544, filed on May 9, 1991, now abandoned.

(51) Int. Cl.⁷ ..................................................... A61K 9/70
(52) U.S. Cl. ..................... 424/445; 424/443; 424/78.06; 424/DIG. 13
(58) Field of Search ..................................... 424/443, 445, 424/78.06, DIG. 13

(56) References Cited

U.S. PATENT DOCUMENTS

| 4,243,656 | | 1/1981 | Walliczek . |
| 4,551,490 | | 11/1985 | Doyle et al. . |
| 4,948,580 | | 8/1990 | Browning . |
| 5,059,189 | * | 10/1991 | Cilento et al. . |
| 5,162,052 | * | 11/1992 | Hoffmann et al. . |

* cited by examiner

*Primary Examiner*—Raj Bawa
(74) *Attorney, Agent, or Firm*—Theodore R. Furman, Jr.; John M. Kilcoyne

(57) ABSTRACT

An absorbent wound filler having high capacity for absorbing wound exudate comprising a polymeric matrix having absorbing powders dispersed within the matrix and method of treating an exudating wound by applying the wound filler to the wound. The absorbing powders contain sodium calcium alginates and also may contain cross-linked sodium carboxymethylcellulose, absorbent polyacrylates and water soluble hydrocolloids.

13 Claims, No Drawings

METHOD AND COMPOSITION FOR ABSORBING WOUND FLUIDS

This is a continuation of U.S. Ser. No. 08/198,026 filed Feb. 17, 1994, now abandoned, which was a continuation-in-part of U.S. Ser. No. 07/990,719 filed Dec. 15, 1992 now abandoned which was a continuation-in-part of U.S. Ser. No. 07/697,544 filed May 9, 1991, now abandoned.

BACKGROUND OF THE INVENTION

1. Field of the Invention

This invention relates to an improved wound filler. More particularly, this invention relates to a wound filler having high moisture absorption capacity.

2. Description of the Prior Art

It is well known that the removal of wound exudates is important to the process of healing of wounds. Commonly used wound dressings utilize gauze, foams, sponges, cotton wads or other fibrous materials. Gauze and other fibrous materials absorb fluids by capillary action. However, gauze and other fibrous materials have the disadvantage in that when new tissue is formed, in the process of healing, it engulfs the fibers of these materials and it is torn when the material is removed causing wound injury on removal.

Various other materials have been used, such as gels, hydrogels, granules and pastes to remove exudates from wounds. These materials have the disadvantage of being difficult to remove from the wound after hydration.

U.S. Pat. No. 4,551,490 describes an adhesive composition useful with ostomy and incontinent appliances and which has also been used in adhesive bandages. The composition consists of a homogeneous mixture of polyisobutylene, styrene radial or block-type copolymer, mineral oil, soluble hydrocolloid gum, water swellable cohesive strengthening agent and a tackifier. This composition has limited exudate absorption capacity and requires a tackifier for its intended use as an adhesive composition.

SUMMARY OF THE INVENTION

The present invention provides wound filler having high exudate absorbing capacity. The wound filler comprises from about 25% to 75% by weight of a polymeric matrix and 25% to 75% by weight of absorbing powders. The polymeric matrix contains from about 15% to 75% by weight of one or more styrene radial or block type copolymers, from about 5% to 40% by weight of one or more polyisobutylenes and from about 5% to 40% of mineral oil. The absorbing powders contain from about 10% to 100% by weight of sodium calcium alginates, from about 0% to 80% by weight of cross-linked sodium carboxymethylcellulose, from about 0% to 80% by weight of absorbent polyacrylates and from about 0% to 20% by weight of water soluble hydrocolloids.

This invention is also directed to a method of wound healing which comprises placing the absorbent wound filler into the wound to absorb the exudate.

The absorbent wound filler of this invention can absorb 500% to 1000% its original weight, can be removed from the wound in one piece and does not cause wound injury on removal. The wound filler keeps the wound bed moist and produces in a wound an environment suitable for healing. The filler absorbs exudate without desiccating or dehydrating the wound bed, freshly generated tissue does not grow into it causing injury on removal. The absorbent wound filler of this invention is particularly useful for chronic heavily exudating wounds with large cavities.

DETAILED DESCRIPTION OF THE INVENTION

The absorbent wound filler of the present invention contains a polymeric matrix and absorbing powers dispersed within the matrix.

The wound filler contains from about 25% to 75% by weight of polymeric matrix and 25% to 75% by weight of absorbing powders. Preferably, the wound filler contains 35% to 50% matrix and 50% to 65% absorbing powders.

The polymeric matrix is the structural component of the wound filler of this invention. It is sponge-like or a network of polymeric stretchable fibers or lamellas, within which the absorbing powders are entrapped. The polymeric matrix is a stretchable, elastic, sponge-like network of long chain molecules which form a mat-like structure. Embedded within this three-dimensional network are absorbing powders, powders capable of hydrating and swelling when exposed to exudate. The polymeric stretchable network allows the hydrating powders to swell and retains the powders in an integral structure but does not disintegrate under the forces of expansion. In addition, the polymeric matrix retains its physical properties when irradiated.

The polymeric matrix contains from about 15% to 75% by weight of styrene radial or block type copolymers and from about 5% to 40% by weight of mineral oil and from about 5% to 40% by weight of polyisobutylene. The preferred polymeric matrix composition contains 40% to 60% styrene radial or block type copolymers and 20% to 30% mineral oil and 20% to 30% polyisobutylenes.

The styrene radial or block copolymer component of the wound filler provides structure and elasticity. The material permits swelling of the absorbent powders and does not break down when exposed to gamma radiation. These materials are described in U.S. Pat. No. 4,551,490. Particularly suitable styrene copolymers include styrene-butadiene-styrene (S-B-S) and styrene-isoprene-styrene (S-I-S) block type copolymers both of which are commercially available, for example, from Shell Chemical Co. under the trademark Kraton, as Kraton 1100, 1101, 1102, 1107, etc. The most preferred material is the styrene-isoprene-stryrene copolymer Kraton 1107. One or more styrene-isoprene-styrene (S-I-S) block type copolymers may be employed.

The polyisobutylene component of the wound filler helps to bind the absorbing powders in the styrene radial or block copolymers network. It is a very viscous semi-solid material. Suitable polyisobutylene materials are described in U.S. Pat. No. 4,551,490. The preferred polyisobutylenes are more low molecular weight polyisobutylenes having a viscosity average molecular weight of from about 36,000 to about 58,000 (Florey). Such polyisobutylenes are commercially available under the trademark Vistanex from Exxon as grades LMMS and LMMH. Preferably, polyisobutylene Vistanex LMMH is used in the wound filler of this invention. If desired, 25% to 75% of the polyisobutylene can be substituted with butyl rubber.

The mineral oil functions as a plasticizer for the styrene radial or block copolymer component. It is also functions to increase the stretchability of the wound filler matrix.

The absorbing powders of the wound filler of the present invention constitute 25% to 75% by weight of the composition. In the preferred compositions, the absorbing powders are present in about 50% to 65%. The powders for use in this invention absorb at least 300% by weight of the wound filler and preferably 500%. The absorbing powders useful in the invention have large water absorbing capacity, i.e., 1000% to 4000% by weight and are capable of being irradiated without substantial loss of water absorbing capacity. Additionally, they must not be easily leached out of the matrix when in contact with water.

The absorbing powders contain from about 10% to 100% by weight of sodium-calcium alginates such as those available under the tradename KELSET from Kelco Co., or mixtures of sodium alginate and calcium alginate commercially available under the tradename SOBALG Na Alginate and SOBALG Ca Alginate and commercially available from Grinsted of Denmark or mixtures of Na Alginate and Ca Alginate available under the tradenames PROTANAL Na Alginate and PROTANAL Ca Alginate from Protan of Norway. Preferably, the absorbing powders contain 10% to 75% by weight of sodium-calcium alginates.

In addition to the alginates, the absorbing powders contain from 0% to 80% and preferably 0% to 60% by weight of cross-linked sodium carboxymethylcellulose such as that commercially available under the tradename AcDiSol from FMC and under the tradename AKUCELL SWX 177 from Akzo Co. of Holland and 0% to 80% and preferably 0% to 60% of finely divided substantially water insoluble highly absorbent polyacrylates representative of the highly absorbent polyacrylates are starch-graft copolymer such as that described in U.S. Pat. No. 3,661,815 and commercially available from Grain Processing Corp. under the tradename WATER LOCK A100 [a starch-graft-poly (sodium acrylate-co-acrylamide)], salt of cross-linked polyacrylic acid/polyalcohol grafted copolymer commercially available under the tradename FAVOR SAB800 from Stockhausen, Inc., Greensboro, N.C., polyacrylate available under the tradename SALSORB 84 from Allied Colloids, Inc., Suffolk, Va., sodium polyacrylate available under the tradename WATER LOCK J500 from Grain Processing Corporation, cross-linked acrylic polymer under the name ARIDALL 1078 from American Colloid Company, Skokie, Ill., and potassium polyacrylate under the name ARASORB 732 and 810 from Arakawa Chemical Industries, Ltd., Osaka, Japan. WATER LOCK A100 is the preferred polyacrylate.

Suitable water soluble hydrocolloids include sodium carboxymethylcellulose, pectin, which is preferred, gelatin, guar gum, locust bean gum, gum karaya and mixtures thereof. The water soluble hydrocolloids are present in an amount of from about 0% to 20% of the weight and preferably 5% to 15%.

The wound filler composition can, if desired, contain small amounts, i.e., less than 1%, of pharmacologically active ingredients. For example, an antibiotic or antimicrobial agent such as neomycin or penicillin, an antiseptic agent such as povidone iodine, an anti-inflammatory agent such as hydrocortisone or triamcinolone acetonides, or a skin protective agent such as zinc oxide can be included in the composition.

The wound filler of this invention is prepared by mixing and heating the styrene copolymers and mineral oil in a heavy duty high shear sigma blade mixer. The mixture is heated from about 125° C. to about 150° C., preferably 150° C., and the mixing is continued until the mass is homogeneous. The mixture is then cooled to 125° C. and polyisobutylene is added and the mixture is mixed until a soft plastic, lightly tacky mass is formed. After cooling to about 100° C., the absorbing powders are added and material is mixed to form a dough-like mass. The doughy mass is calandered through a double roll mill between two sheets of release paper at 100° C. to 125° C., preferably, about 125° C. A flexible sheet or slab of any desired thickness (20, 40, 60, 80, 100 mils depending on the gap set between the two rolls) is formed, 40 to 60 mils thickness is desired. The slabs are die cut to any desired size and shape, sealed in pouches and may be sterilized by means of gamma radiation.

The following examples are intended to illustrate the invention described herein without unduly restricting it.

EXAMPLE 1

Absorbent wound filler was prepared having the following composition:

|  | Weight Percent Of Wound Filler |
|---|---|
| Polyisobutylene (Vistamex LMMH) | 10 |
| Styrene-isoprene-styrene copolymer (Kraton 1107) | 20 |
| Mineral Oil | 10 |
| Pectin | 10 |
| Na Ca Alginates | 25 |
| Cross-linked sodium carboxymethylcellulose (Ac-Di-Sol) | 25 |
|  | 100 |

Kraton (60 g) is mixed with mineral oil (30 g) in a sigma blade mixer at 150° C. Polyisobutylene (30 g) is added and mixed after cooling to 125° C. for ten minutes. A soft plastic mass is formed. The mixture is cooled to 100° C. and pectin (30 g), Na Ca Alginates (75 g) and cross-linked sodium carboxymethylcellulose (75 g) are added and mixed at 100° C. for 30 minutes until a homogeneous dough-like mass is obtained.

The doughy mass is calandered through a double roll mill between two sheets of release paper at 125° C. A flexible slab of 60 mils is formed.

The slabs are die cut to 1"×2", 2"×2" and 2"×3" and circular discs of 1", 2" and 3" diameter and sealed in pouches and gamma irradiated at 2.5 MR.

The moisture absorption of the absorbent wound filler is determined according to the following procedure:

(1) Samples of 1"×21" are weighed and placed into sealed cups full of saline solution at 40° C.

(2) Periodically the samples are removed from the solution, patted dry on a towel to remove superficial water, weighed, placed back into the cups.

(3) The weights are taken at 0.25, 0.5, 1.0, 2.0, 4.0, 8.0, 24.0 hours initially, and then daily for one week.

(4) The moisture absorption is expressed in percent of initial weight and it is calculated by the following formula:

$$\% \text{ Moist Absorption} = \frac{Wt - Wi}{Wi} \times 100$$

Wt=Weight at various times
Wi=Initial Weight

When the absorbent wound filler of this Example (irradiated and non-irradiated) is tested for moisture absorption according to the above procedure the following results are obtained:

| Water Absorption Capacity (% of Initial Weight) | | | | | | | | |
|---|---|---|---|---|---|---|---|---|
| Time (Hours) | 2 | 6 | 8 | 24 | 48 | 144 | 216 | 312 |
| Sample | | | | | | | | |
| Irradiated | 84 | 271 | 313 | 465 | 543 | 589 | 580 | 541 |
| Non-Irradiated | 67 | 255 | 315 | 564 | 656 | 716 | 716 | 702 |

EXAMPLE 2

Absorbent wound filler was prepared having the following composition:

| | Weight Percent Of Wound Filler |
|---|---|
| MATRIX 45% | |
| Polyisobutylene (Vistamex LMMI) | 11.25 |
| Styrene-isoprene-styrene copolymer (Kraton 1107) | 22.5 |
| Mineral Oil | 11.25 |
| POWDERS 55% | |
| Pectin | 10 |
| Na Ca Alginates (Kelset) | 15 |
| Starch graft copolymer - (WATERLOCK A100) | 30 |
| | 100 |

Kraton (67.50 g) is mixed with mineral oil (33.75 g) in a sigma blade mixer at 150° C. Polyisobutylene (33.75 g) is added and mixed after cooling to 125° C. for ten minutes. A soft plastic mass is formed. The mixture is cooled to 100° C. and pectin (30.00 g), Na Ca Alginates (45.00 g) and starch graft copolymer (polyacrylate and polyacrylamide) are added and mixed at 100° C. for 30 minutes until a homogeneous dough-like mass is obtained.

A prior art medical adhesive formulation as disclosed in U.S. Pat. No. 4,551,490 was prepared as described in Example 18 of that patent and had the following composition:

| Matrix | Weight % of Adhesive |
|---|---|
| Polyisobutylene (Vistanex LMMH) | 8.00 |
| Butyl Rubber 065 | 16.25 |
| Styrene-isoprene-styrene copolymer (Kraton 1107) | 6.00 |
| Antioxidant (Irgonox 1010) | 0.50 |
| Mineral Oil | 11.50 |
| Tackifier (Pentalyn H) | 12.75-- |
| --Hydrocolloids and Strengthening Agents (45%) | |
| Pectin | 15.00 |
| Gelatin | 15.00 |
| Na Carboxymethylcellulose | 15.00 |
| | 100.00-- |

The doughy mass is calandered through a double roll mill between two sheets of release paper at 125° C. A flexible slab of a desired thickness of 60 mils is formed.

The slabs are die cut to 1"×2", 2"×2" and 2"×3" and circular discs of 1", 2" and 3" diameter and sealed in pouches and gamma irradiated at 2.5 MR.

When the absorbent wound filler of this Example 2 and the prior art medical adhesive above are tested for moisture absorption according to the procedure described in Example 1, the following results are obtained:

| | Rate of Absorption Average of Results | |
|---|---|---|
| Time Interval | % Weight Gain Present Wound Filler | Prior Art Adhesive |
| 15 minutes | 92% | Not Tested |
| 30 minutes | 147% | Not Tested |
| 1 hour | 258% | 7.5% |
| 2 hours | 469% | 10.3% |
| 4 hours | 629% | 14.3% |
| 6 hours | Not Tested | 15.2% |
| 8 hours | 743% | Not Tested |
| 24 hours | 818% | 66.6% |
| 48 hours | 858% | 164% |
| 72 hours | 870% | 178% |
| 96 hours | 916% | 157% |
| 120 hours | 956% | Not Tested-- |

EXAMPLE 3

Absorbent wound filler was prepared having the following composition:

| | Weight Percent Of Wound Filler |
|---|---|
| MATRIX 40% | |
| Polyisobutylene (Vistamex LMMH) | 10 |
| Styrene-isoprene-styrene copolymer (Kraton 1107) | 20 |
| Mineral Oil | 10 |
| POWDERS 60% | |
| Pectin | 10 |
| Na Ca Alginates (Kelset) | 20 |
| Cross-linked sodium carboxymethylcellulose (Ac-Di-Sol 15%, Akucell SW x 177 15%) | 30 |
| | 100 |

Kraton (60.00 g) is mixed with mineral oil (30.00 g) in a sigma blade mixer at 150° C. Polyisobutylene (30.00 g) is added and mixed after cooling to 125° C. for ten minutes. A soft plastic mass is formed. The mixture is cooled to 100° C. and pectin (30.00 g), Na Ca Alginates (60.00 g) and cross-linked sodium carboxymethylcellulose (90.00 g) are added and mixed at 100° C. for 30 minutes until a homogeneous dough-like mass is obtained.

The doughy mass is calandered through a double roll mill between two sheets of release paper at 125° C. A flexible slab of a desired thickness of 60 mils is formed.

The slabs are die cut to 1"×2", 2"×2" and 2"×3" and circular discs of 1", 2" and 3" diameter and sealed in pouches and gamma irradiated at 2.5 MR.

When the absorbent wound filler of this Example (irradiated) is tested for moisture absorption according to the procedure described in Example 1 the following results are obtained:

| RATE OF ABSORPTION AVERAGE OF RESULTS | |
|---|---|
| Time Interval | % Weight Gain |
| 15 minutes | 60% |
| 30 minutes | 88% |
| 1 hour | 142% |
| 2 hours | 244% |
| 4 hours | 327% |
| 8 hours | 393% |
| 24 hours | 466% |
| 48 hours | 502% |
| 72 hours | 534% |
| 96 hours | 542% |
| 120 hours | 545% |

EXAMPLES 4–10

Following the procedure described in Example 1 and using the formulations shown in Table I, seven absorbent wound fillers were prepared and wound fillers of Examples 5, 6, 7 and 8 evaluated for moisture absorption according to the procedure described in Example 1. The moisture absorption test results are set forth in Table II.

TABLE I

| EXAMPLE | Polymeric Matrix | Pectin | Na Ca Alginates | Crosslinked Na CMC | Water Lock A100 |
|---|---|---|---|---|---|
| 4 | 40 [1] | | | 60 | |
| 5 | 40 [1] | | | 10 | 50*** |
| 6 | 40 [1] | 10 | | 40 | 10 |
| 7 | 40 [1] | 10 | | 50 | |
| 8 | 45 [2] | 10 | | 22.5 | 22.5* |
| 9 | 40 [1] | 10 | | 25 | 25** |
| 10 | 40 [1] | 10 | | 20 | 30*** |

[1] Polymeric matrix is the same as that of Example 1
[2] Polymeric matrix is the same as that of Example 2
* AcDiSol
** Akucell x177
*** A blend of equal parts of AcDiSol and Akucell x177

EXAMPLE 11

The following results were obtained from wound studies conducted on pigs:

| | % INCREASE IN WEIGHT OF WOUND FILLER | | | |
|---|---|---|---|---|
| Sample | DAY 1 | DAY 2 | DAY 4 | DAY 7 |
| EXAMPLE 2 | 468 | 426 | 449 | 285 |
| EXAMPLE 10 | 341 | 306 | 390 | 264 |

15 mm dia.×1.75 mm thick discs of the wound filler of Examples 2 and 10 were placed in 25 mm dia.×5 mm depth wounds and covered with a 4"×4" dressing. Initially and at the end of days 1, 2 and 4 the wound filler was weighed and replaced with a fresh dry wound filler disc; at the end of day 7 the wound filler was weighed but not replaced. The percent increase of weight was calculated.

The wound fillers of the present invention absorb large quantities of wound exudate. In the process of absorbing fluids they swell and fill the wound cavity. They can absorb 500% to 1000% of their original weight and swell proportionally, i.e., they can swell 5–10 times their original volume. The wound fillers absorb by hydration and can be removed from the wound in one piece. They do not cause wound injury on removal and keep the wound bed moist and in an environment suited for healing without desiccating or dehydrating the wound bed. The wound fillers do not adhere to the wound bed and freshly generated tissue does not grow into the filler causing injury on removal. Their main application is directed to chronic heavily exudating wounds, with large cavities, where absorption and filling are indicated. The wound filler also finds use in treatment of ulcers, burns, pressure sores, etc.

The wound filler of any desired thickness is applied to the wound. Usually ⅕ to ¼ of the wound cavity is filled with a small piece of wound filler and the wound sealed with an occlusive dressing. As exudate is generated it is absorbed by the wound filler which swells to fill the entire wound cavity. Usually the wound filler will not be required to be replaced for several days.

Thus it is apparent from the foregoing description that the objects of this invention have been attained. A novel absor-

TABLE II

| | Water Absorption Capacity (% of Initial Weight) | | | | | | | | |
|---|---|---|---|---|---|---|---|---|---|
| Time (Hours) | 2 | 4 | 6 | 8 | 24 | 48 | 120 | 144 | 216 | 312 |
| EXAMPLE 5 | | | | | | | | | | |
| Irradiated | 138 | | 401 | 419 | 551 | 612 | | 704 | 658 | 539 |
| Non-Irradiated | 97 | | 287 | 300 | 363 | 386 | | 427 | 413 | 369 |
| EXAMPLE 6 | | | | | | | | | | |
| Irradiated | | 453 | | 537 | 662 | 688 | 687 | 883 | | |
| Non-Irradiated | | 412 | | 644 | 854 | 911 | 1413 | 1572 | | |
| EXAMPLE 7 | | | | | | | | | | |
| Irradiated | | 237 | | 412 | 516 | 564 | 616 | 621 | | |
| Non-Irradiated | | 352 | | 610 | 765 | 842 | 911 | 922 | | |
| EXAMPLE 8 | | | | | | | | | | |
| Irradiated | | 83 | | 258 | 297 | 429 | 493 | | 555 | 562 | 543 |
| Non-Irradiated | | 94 | | 270 | 326 | 552 | 615 | | 672 | 644 | 610 | bent wound filler has been invented which has high absorbing capacity. In addition, a novel method of treating wounds has been invented.

While this invention has been described and exemplified in terms of its preferred embodiment, those skilled in the art will appreciate that modifications can be made without departing from the spirit and scope of this invention.

We claim:

1. An absorbent wound filler composition having an absorbence capacity of at least 300% based on initial weight of said wound filler which consists essentially of:
   (a) from about 25% to 75% by weight of a polymeric matrix wherein said matrix consists of
      (i) from about 15% to 75% by weight of one or more styrene radial or styrene-butadiene-styrene or styrene-isoprene-styrene block copolymers;
      (ii) from about 5% to 40% by weight of one or more ployisobutylenes; and
      (iii) from about 5% to 40% by weight of mineral oil; and
   (b) from about 25% to 75% by weight of absorbing powders dispersed within said matrix wherein said absorbing powders consist of
      (i) from about 10% to 100% by weight of sodium calcium alginates;
      (ii) from about 0% to 80% by weight of cross-linked sodium carboxymethylcellulose;
      (iii) from about 0% to 80% by weight of absorbent polyacrylates; and
      (iv) from about 0% to 20% by weight of water soluble hydrocolloids.

2. The absorbent wound filler of claim 1 wherein said wound filler comprises from about 35% to 50% polymeric matrix and from about 50% to 65% absorbing powders.

3. The absorbent wound filler of claim 1 wherein the absorbent polyacrylate is a starch-graft poly (sodium acrylate-co-acrylate) copolymer.

4. The absorbent wound filler of claim 1 wherein the water soluble hydrocolloid is pectin.

5. The absorbent wound filler of claim 2 wherein said absorbing powders comprise from about 10% to about 30% by weight of Na Ca alginates.

6. The absorbent wound filler of claim 1 wherein said wound filler composition consists of:
   (a) about 20% by weight of styrene-isoprene-styrene copolymer;
   (b) about 10% by weight of polyisobutylene;
   (c) about 10% by weight of mineral oil;
   (d) about 25% by weight of Na Ca alginates;
   (e) about 25% by weight of cross-linked sodium carboxymethylcellulose; and
   (f) about 10% by weight of pectin.

7. The absorbent wound filler of claim 1 wherein said wound filler composition consists of:
   (a) about 22.5% by weight of styrene-isoprene-styrene copolymer;
   (b) about 11.25% by weight of polyisobutylene;
   (c) about 11.25% by weight of mineral oil;
   (d) about 15% by weight of Na Ca alginates;
   (e) about 30% by weight of starch-graft poly(sodium acrylate-co-acrylate); and
   (f) about 10% by weight of pectin.

8. The absorbent wound filler of claim 1 wherein said wound filler composition consists of:
   (a) about 20% by weight of styrene-isoprene-styrene copolymer;
   (b) about 10% by weight of polyisobutylene;
   (c) about 10% by weight of mineral oil;
   (d) about 20% by weight of Na Ca alginates;
   (e) about 30% by weight of cross-linked sodium carboxymethylcellulose; and
   (f) about 10% by weight of pectin.

9. The absorbent wound filler of claim 1 wherein said wound filler composition consists of:
   (a) about 20% by weight of styrene-isoprene-styrene copolymer;
   (b) about 10% by weight of polyisobutylene;
   (c) about 10% by weight of mineral oil;
   (d) about 10% by weight of Na Ca alginates; and
   (e) about 50% by weight of cross-linked sodium carboxymethylcellulose.

10. The absorbent filler of claim 1 wherein said wound filler composition consists of
    (a) about 20% by weight of styrene-isoprene-styrene copolymer;
    (b) about 10% by weight of polyisobutylene;
    (c) about 10% by weight of mineral oil;
    (d) about 40% by weight of Na Ca alginates;
    (e) about 10% by weight of starch-graft poly(sodium acrylate-co-acrylate); and
    (f) about 10% by weight of pectin.

11. The absorbent filler of claim 1 wherein said wound filler composition consists of
    (a) about 20% by weight of styrene-isoprene-styrene copolymer;
    (b) about 10% by weight of polyisobutylene;
    (c) about 10% by weight of mineral oil;
    (d) about 50% by weight of Na Ca alginates;
    (e) about 10% by weight of pectin.

12. The absorbent filler of claim 1 wherein said wound filler composition consists of
    (a) about 22.5% by weight of styrene-isoprene-styrene copolymer;
    (b) about 11.25% by weight of polyisobutylene;
    (c) about 11.25% by weight of mineral oil;
    (d) about 22.5% by weight of Na Ca alginates;
    (e) about 22.55% by weight of cross-linked sodium carboxymethylcellulose; and
    (f) about 10% by weight of pectin.

13. A method of treating an exudating wound, which comprises applying an absorbent wound filler composition having an absorbence capacity of at least 300% based on initial weight of said wound filler to said wound, and having a swelling capacity proportional to the absorbing capacity whereby in absorbing and swelling said wound filler fills the wound cavity, wherein said wound filler composition consists essentially of:
    (a) from about 25% to 75% by weight of a polymeric matrix wherein said matrix consists of
       (i) from about 15% to 75% by weight of one or more styrene radial or styrene-butadiene-styrene or styrene-isoprene-styrene block copolymers;
       (ii) from about 5% to 40% by weight of one or more polyisobutylenes; and
       (iii) from about 5% to 40% by weight of mineral oil; and (b) from about 25% to 75% by weight of absorbing powders dispersed within said matrix wherein said absorbing powders consist of
  (i) from about 10% to 100% by weight of sodium calcium alginates;
  (ii) from about 0% to 80% by weight of cross-linked sodium carboxymethylcellulose;
  (iii) from about 0% to 80% by weight of absorbent polyacrylates; and
  (iv) from about 0% to 20% by weight of water soluble hydrocolloids; and covering the wound and absorbent wound filler with an occlusive dressing.

* * * * *